(12) United States Patent
Vainshtein et al.

(10) Patent No.: US 8,479,567 B2
(45) Date of Patent: Jul. 9, 2013

(54) DEVICE AND METHOD OF PARTICLE FOCUSING

(75) Inventors: Peter Vainshtein, Haifa (IL); Michael Shapiro, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 648 days.

(21) Appl. No.: 12/698,193

(22) Filed: Feb. 2, 2010

(65) Prior Publication Data

US 2010/0192678 A1    Aug. 5, 2010

Related U.S. Application Data

(60) Provisional application No. 61/149,061, filed on Feb. 2, 2009.

(51) Int. Cl.
*G01N 15/06*    (2006.01)

(52) U.S. Cl.
USPC ........................................ 73/61.75; 73/61.71

(58) Field of Classification Search
USPC ................................ 73/61.71, 61.75; 137/803
See application file for complete search history.

(56) References Cited

U.S. PATENT DOCUMENTS

2009/0178716 A1 *   7/2009   Kaduchak et al. .............. 137/13

OTHER PUBLICATIONS

Vainshtein et al. "Focusing in a Quadrupole Acoustic Channel", Aerosol Science, 40: 707-719, 2009.

* cited by examiner

*Primary Examiner* — Hezron E Williams
*Assistant Examiner* — Paul West

(57) ABSTRACT

A method of focusing a plurality of discrete particles. The method comprises establishing a flow of a fluid medium carrying a plurality of discrete particles within a capillary having a plurality of separate walls and a longitudinal axis. The method further includes vibrating the plurality of separate walls to apply an acoustic field having a central axis substantially along the longitudinal axis to focus the plurality of discrete particles substantially along the longitudinal axis.

10 Claims, 7 Drawing Sheets

DEVICE AND METHOD OF PARTICLE FOCUSING

RELATED APPLICATIONS

This application claims the benefit of priority of U.S. Provisional Patent Application No. 61/149,061, filed on Feb. 2, 2009, the contents of which are incorporated by reference as if fully set forth herein.

FIELD AND BACKGROUND OF THE INVENTION

The present invention, in some embodiments thereof, relates to a particle focusing and, more particularly, but not exclusively, to methods and systems of acoustic focusing.

Aerodynamic focusing is a mechanism that has been widely used to produce particle beams, for example tightly collimated particle beams. Using the aerodynamic lenses, near-axis particles can be focused onto a streamline in principle. An aerodynamic lens system typically consists of three parts: a flow control orifice, focusing lenses, and an acceleration nozzle. The choked inlet orifice fixes the mass flow rate through the system and reduces pressure from ambient to the value required to achieve aerodynamic focusing. The focusing lenses are a series of orifices contained in a tube that create converging-diverging flow accelerations and decelerations, through which particles are separated from the carrier gas due to their inertia and focused into a tight particle beam. The accelerating nozzle controls the operating pressure within the lens assembly and accelerates particles to downstream destinations. Aerodynamic lenses have been widely used in particle mass spectrometers. Available designs for aerodynamic lenses effectively collimate particles as small as 30 nm.

At present, focusing of a range of micron and submicron size aerosol particles is carried out using aerodynamic forces in periodic aerodynamic lens arrays, see Liu, P., Ziemann, P. J., Kittelson, D. B. and McMurry, P. H. (1995) Aerosol Sci. Techn., 22, 293-3 13 and Wang, X., Gidwani, A., Girshick, S. L. and McMurry, P. H. (2005). Aerosol Sci. Techn., 39, 624-636., which are incorporated herein by reference. Such arrays are used as inlets to on-line single-particle analyzers; see Wexler, A. S. and Johnston, M. V. (2001) in Aerosol Measurement: Principles, Techniques, and Applications. P. A. Baron and K. Willeke ed., Wiley, New York, which is incorporated herein by reference.

Hydrodynamic focusing is a technique usually used to provide results from flow cytometers or Coulter counters for determining the size of bacteria or cells. When using Hydrodynamic focusing for flow cytometry microscopic particles, such as cells and chromosomes, are counted and examined by suspending them in a stream of fluid and passing them by an electronic detection apparatus.

Acoustic focusing, such as Acoustic cytometry, is a technology that is used for focusing cells or particles with acoustic radiation pressure forces. For example acoustic focusing is employed in flow cytometry analysis, either as a substitute for hydrodynamic focusing or in combination with it, is described in Curr. Protoc. Cytom. 49:1.22.1-1.22.12. © 2009 by John Wiley & Sons, Inc, which is incorporated herein by reference. The use of acoustic standing waves to concentrate initially homogeneously suspended aerosol or hydrosol particles in acoustic pressure nodal or antinodal planes was first visualized by Kundt (1866) and then described by and Rayleigh (1945). Subsequent works utilize this phenomenon (see Duhin, 1960; Czyz, H., 1990; Dain et al., 1995; Vainshtein et al., 1996 and papers cited therein) for various applications.

The acoustic force was also used to position and levitate particles (see King, 1934; Fuchs, 1964; Coakley et al., 1989; Gopinath and Mills, 1994; Hertz, 1995 and papers cited therein). In those works the particle motion was studied in situations when undisturbed fluid was at rest. A number of devices and method have been used to use acoustic waves to concentrate aerosol or hydrosol particles. An example of using acoustic focusing technology is described in U.S Patent Application Publication number 2010/0009333, filed on 17 Jun. 2009 that describes methods for using acoustic focusing technology on its own or in conjunction with hydrodynamic focusing for analyzing biological samples. In one application, a preferential orientation of biological particles is achieved by applying a substantially elliptical acoustic field. The application describes a sample comprising a fluid medium carrying a plurality of discrete biological particles which are pre-concentrated in-line with a sample analyzer, such as a flow cytometer, where a sheath fluid is introduced after acoustic pre-concentration. The application describes methods for acoustically separating suspended discrete biological particles of different densities from a fluid medium.

SUMMARY OF THE INVENTION

According to some embodiments of the present invention there is provided a method of focusing a plurality of discrete particles. The method comprises establishing a flow of a fluid medium carrying a plurality of discrete particles within a capillary having a plurality of separate walls and a longitudinal axis and vibrating the plurality of separate walls to apply an acoustic field having a central axis substantially along the longitudinal axis, the acoustic field focusing the plurality of discrete particles substantially along the longitudinal axis.

Optionally, the plurality of separate walls are separately vibrated in a frequency of less than 10 Mega Hertz (10 MHZ).

Optionally, the acoustic field is a substantially quadrupole acoustic field.

Optionally, the method comprises analyzing signals received from the particles, substantially along the longitudinal axis, to identify at least one characteristic of the plurality of discrete particles.

Optionally, the acoustic field creates a plurality of streamlines each between two adjacent walls of the plurality of separate walls; the applying comprises maneuvering the plurality of particles along the streamlines, toward the longitudinal axis.

Optionally, the vibrating comprises maneuvering each the particle in oscillating motions toward the longitudinal axis.

Optionally, the plurality of particles are plurality of discrete particles.

Optionally, the plurality of separate walls form a substantially unpartitioned inner lumen.

Optionally, the vibrating comprising vibrating plurality of separate walls are separately vibrated in a frequency of about 1 Kilo Hertz (1 KHz).

According to some embodiments of the present invention there is provided a device of focusing a plurality of particles. The device comprises a capillary having a longitudinal axis and a substantially unpartitioned lumen to flow a fluid medium having a plurality of particles and at least one vibration source for vibrating the capillary in a frequency of less than 10 Mega Hertz (MHz) so as to focus the plurality of particles along the longitudinal axis.

Optionally, the inner lumen having a diameter of about 10 millimeter.

Optionally, the capillary having a plurality of separate walls and a plurality of slits, each the slit being formed between each adjacent pair of walls of the plurality of separate walls.

More optionally, the plurality of separate walls are separated from one another.

More optionally, each the vibration source is connected to vibrate one of the plurality of separate walls.

More optionally, each separate wall is convex toward a longitudinal axis of the capillary.

More optionally, each separate wall is concave toward a longitudinal axis of the capillary.

More optionally, the at least one vibration source comprises a plurality of vibration sources arranged to vibrate the capillary so as to form a quadrupole acoustic field having a central axis substantially along a longitudinal axis of the capillary.

Optionally, the capillary having four plurality of separate walls arranged to form a cylindrical lumen.

An aerodynamic lens array having the aforementioned device as a lens in at least one stage.

A single-particle analyzer having the aforementioned device for focusing the plurality of particles before an analysis thereof.

According to some embodiments of the present invention there is provided a device of focusing a plurality of particles. The device comprises a capillary having a longitudinal axis and a plurality of walls sized and shaped to flow a fluid medium having a plurality of particles and a plurality of vibration sources each separately vibrates one of the plurality of walls so as to focus the plurality of particles along the longitudinal axis.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
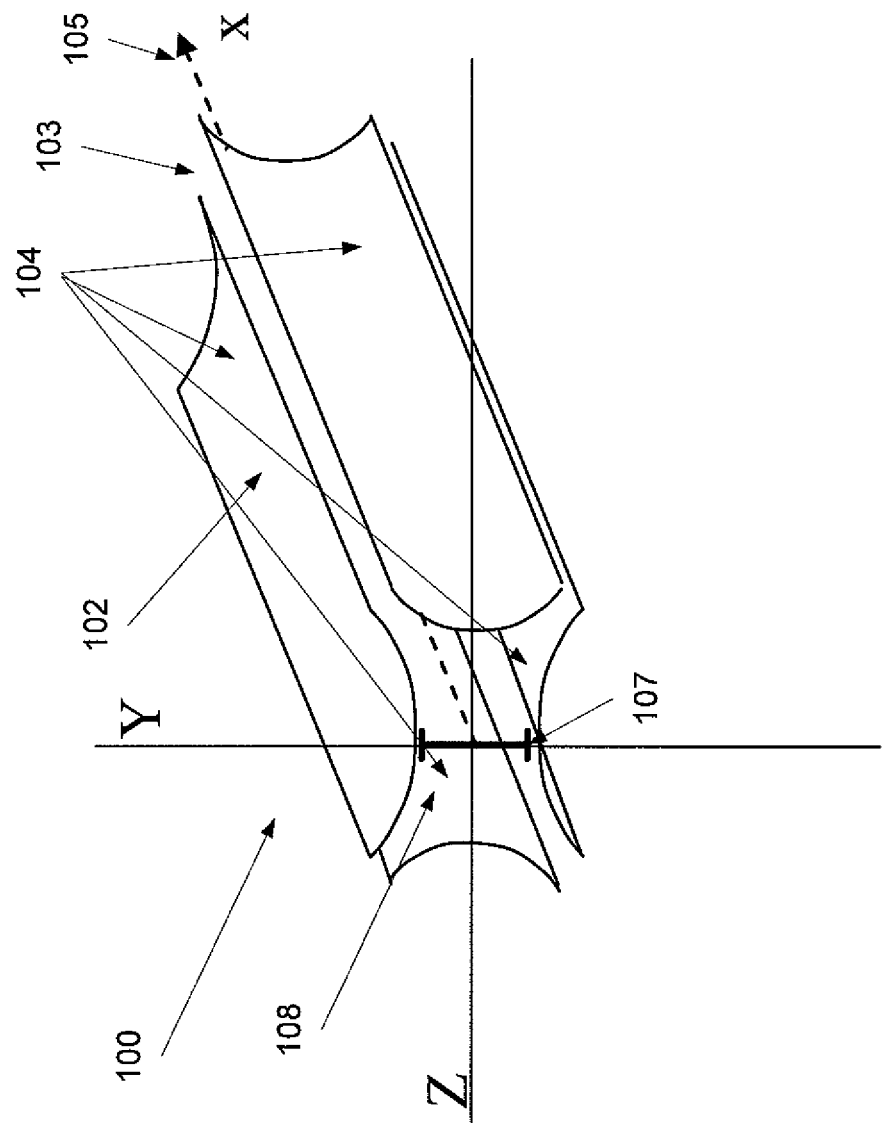
FIG. 1 is a schematic illustration of an exemplary capillary having for separate walls, convex toward the longitudinal axis of said exemplary capillary, according to some embodiments of the present invention.
Figure 2:
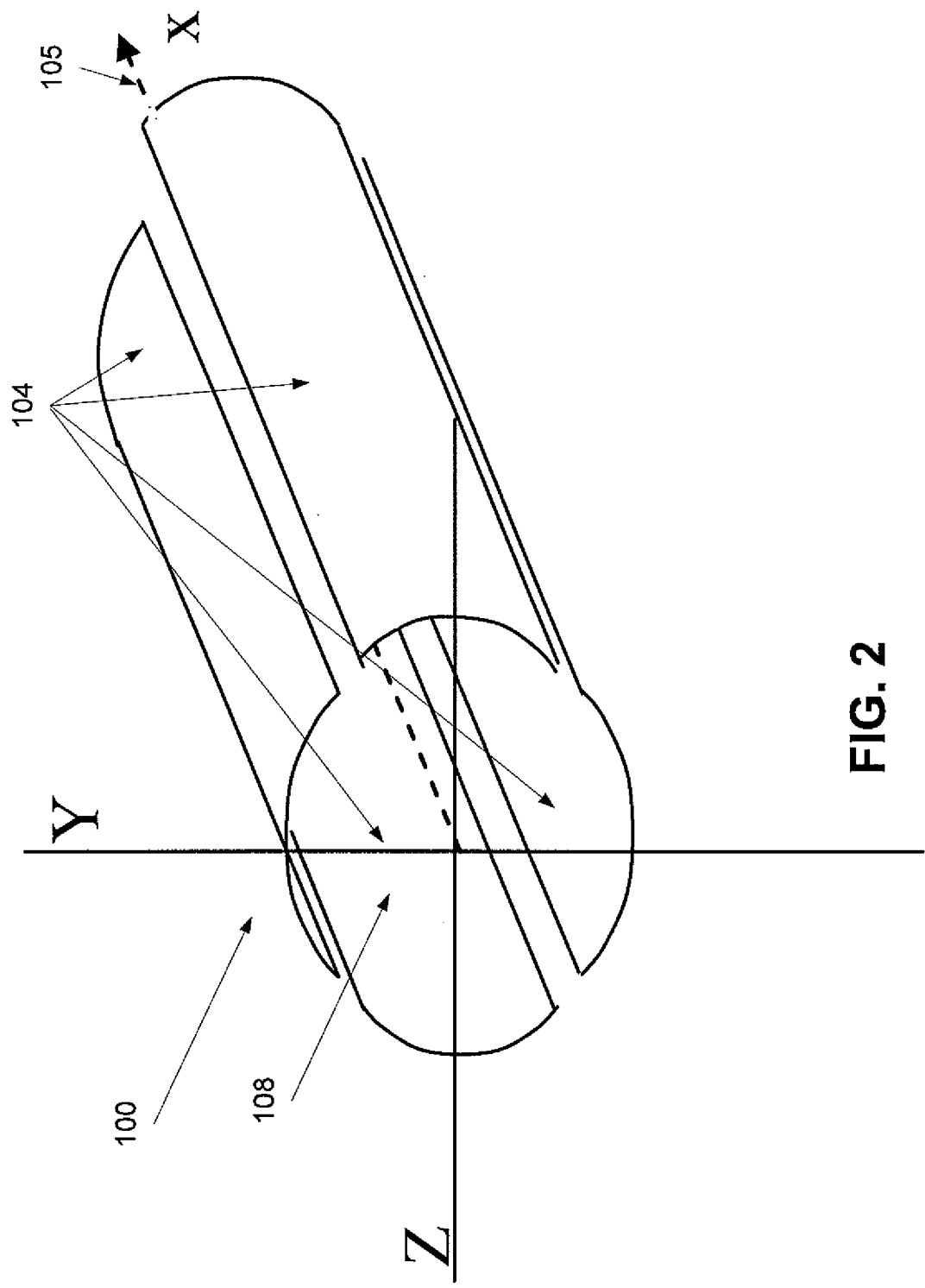
FIG. 2 is a schematic illustration of another exemplary capillary having for separate walls, concave toward the longitudinal axis of said exemplary capillary, according to some embodiments of the present invention.
Figure 3:
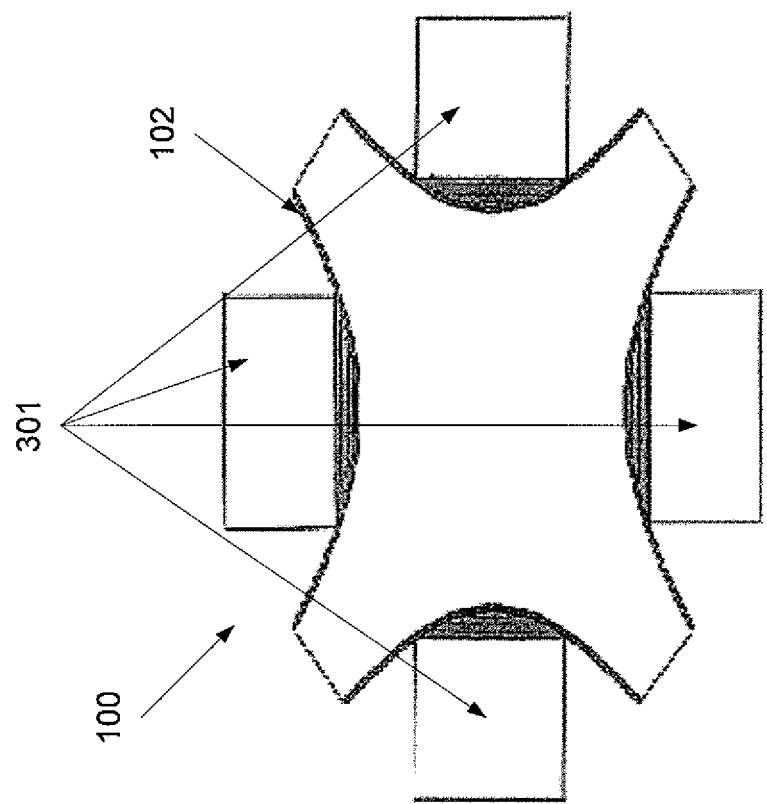
FIG. 3 is a cross sectional schematic illustration of an exemplary capillary having temping drills of vibration sources, according to some embodiments of the present invention.

The present invention, in some embodiments thereof, relates to a particle focusing and, more particularly, but not exclusively, to methods and systems of acoustic focusing.

According to some embodiments of the present invention there is provided method and device of focusing a plurality of discrete particles in a fluid flow capillary. The method is based on establishing a flow of a fluid medium carrying a plurality of discrete particles within a capillary having a plurality of walls, for example 4 walls, optionally separated from one another. The focusing is performed by vibrating the walls, optionally separately, to apply an acoustic field having a central axis substantially along the longitudinal axis of the capillary. The acoustic field focuses the discrete particles substantially along the longitudinal axis. Optionally, the capillary is sized and shaped to apply the acoustic field by wall vibrations in a frequency of less than 10 Mega Hertz (MHz), for example less than 1 MHz, less than 20 KHz, such as about 1 KHz. In such a manner, sensitive particles, such as cells and bacteria, may be concentrated without damage, or without a substantial damage. Optionally, the acoustic field is a quadrupole acoustic field having a central axis substantially along the longitudinal axis of the capillary. Optionally, the walls of the capillary are concave and/or convex toward the longitudinal axis.

According to some embodiments of the present invention, there is provided a device of focusing a plurality of particles. The device comprises a capillary having a substantially unpartitioned lumen and one or more vibration sources for vibrating the capillary in a frequency of less than 10 MHz, for example less than 1 MHz, so as to focus the plurality of particles by creating an acoustic field.

According to some embodiments of the present invention there is provided a device of focusing particles having a capillary with a plurality of separate walls which are sized and shaped to flow a fluid medium having the particles. The device further includes a plurality of vibration sources which are designed to vibrate separately each one of the separate walls so as to focus the plurality of particles by creating an acoustic field, optionally substantially quadrupole.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1 which is a schematic illustration of a device 100 of focusing a plurality of discrete aerosol and/or hydrosol particles by an acoustic field, according to some embodiments of the present invention. The device 100 includes a capillary 102 for conducting flowing fluid, such as liquid or gas, optionally by a pump that is connected thereto. As used herein, a capillary means a channel or chamber having a cylindrical or quasi cylindrical shape having a base selected from rectangular, square, elliptical, oblate circular, round, octagonal, heptagonal, hexagonal, pentagonal, and/or triangular. The shape of the interior walls of the capillary 102 may or may not be the same as the shape of the exterior walls.

The capillary 102 is optionally an unpartitioned capillary 102 that is not divided to chambers. In such a manner, particles which flow in the capillary 102 can easily be washed out from the capillary 102. In such an unpartitioned capillary, contaminations are avoided or reduced as particles are not accumulated in around edges of the partitions. Thus, an analysis of a beam of particles generated by the device 100 is more accurate and/or stable than the analysis of a beam of particles generated by a similar device with a plurality of chambers in its inner lumen.

According to some embodiments of the present invention, as shown at FIG. 1, the capillary 102 has a plurality of separate walls 104, optionally 4. A slit is formed in parallel, or substantially in parallel, to the longitudinal axis 105 of the capillary 102, between each adjacent pair of the walls, as shown at 103.

Optionally, each separate wall is convex toward the longitudinal axis 105, as shown at FIG. 1. Optionally, each separate wall is concave toward the longitudinal axis 105, as shown at FIG. 2.

One or more vibration sources for vibrating the unpartitioned capillary are connected to the separate walls 104. Optionally, as further described below, the vibrating is performed in a frequency of less than 10 Mega Hertz (MHz), for example less than 1 MHz, less than 20 Kilo Hertz (KHz), for instance about 1 KHz. Each vibration source may be a transducer. It should be noted that vibrating the capillary 102 with low frequency sound waves, such as about 1 KHz causes low attenuation.

Optionally, the diameter of the inner lumen 107 of the capillary is about 10 millimeter (mm). In Goddard, G. and Kaduchak, G. (2005) J. Acoust. Soc. Am., 117 (6), 3440-3447 and Goddard, G., Martin, J. C., Graves, S. W (hereinafter: "Goddard et al."), and Kaduchak, G. (2006) Cytometry A, 69, 66-74, which are incorporated herein by reference, particles have been focused acoustically in a liquid flow in a capillary having an inner lumen 108 of 10 mm 107. The device 100 allows focusing particles in a gas flow and/or a liquid flow streamed in a capillary having an inner lumen 108 of 10 millimeter (mm) 107. The particles are concentrated in a beam substantially along the longitudinal axis 105. In such an embodiment, the device 100 is used as aerodynamic lens arrays having a size in the order of 10 mm. It should be noted that the high frequency of ultrasound waves which are applied in used by Goddard et al. are not applicable to particle focusing of particles in a gas flow as it induces strong sound attenuation, see Krasilnikov, V. A. and Krylov, V. V. (1984) Introduction to Physical Acoustics, Nauka (in Russian), which is incorporated herein by reference.

Optionally, the device 100 has a separate vibration source for separately vibrating each wall 104. Reference is now also made to FIG. 3, which is a cross sectional schematic illustration of an exemplary capillary, such as the exemplary capillary 102 depicted in FIG. 1, having temping drills of vibration sources 301, according to some embodiments of the present invention. FIG. 3 depicts exemplary locations of the temping drills 301. Optionally, substrates are used to attach the drills 301 to the walls 104. Optionally, flexible flanges are used to facilitate the vibrations of the walls 104.

In the embodiment depicted in FIG. 3, magnetostrictive transducers 301 are used to produce an acoustic field in the capillary 102. Each transducer consists of a number of magnetostrictive plates which are arranged in parallel to one another. Each transducer 301 is attached to the bottom of the surface of one of the walls 104. For example, the magnetostrictive transducers 301 are ETREMA standard actuator made by ETREMA Products, Inc., which are mounted to vibrate each of the walls 104, for example model 200 of ETREMA Products, Inc. These actuators vibrate the walls with a frequency of about 1 KHz with a stroke of about ±100 μm. Though these actuators are fairly large, about 35 cm long, its tamping drill is of 8.5 mm with pitch of 1 mm and optical density (OD) of 9.53 mm. In such a manner, they fit well to the size of the walls 104 and can be easily attached to vibrate each one of the walls 104, for example as shown at FIG. 3. Optionally, a pair of the walls 104, which are opposite to one another, contract and expand suspension-filled channel interior in phase and a pair of the walls 104, which are adjacent to one another, act in a counter-phase. In such a manner, a quadrupole excitation of fluid oscillations inside the capillary 102 is accomplished. As outlined above and described below, the vibration of the walls 104 focuses particles, such as initially diluted aerosol and/or hydrosol particles, in a fluid medium that is delivered into the capillary 102 for example by a pump connected thereto.

As further described below, this arrangement of vibration sources allows forming a quadrupole acoustic field having a central axis substantially along the longitudinal axis 105 of the capillary 105. For clarity, the use of acoustic waves to concentrate initially homogeneously suspended aerosol or hydrosol particles in acoustic pressure nodal or antinodal planes is visualized in Kundt, A. (1866) Ann. Phys. and Chem. 127, 4, 497 and then described in Rayleigh, Lord (1945) Theory of Sound, Vols 1 an 2, 2nd Edn. Dover, which are incorporated herein by reference. The utilization of this phenomenon is described in Damn, Y., Fichman, M., Gutfinger, C., Pnueli D., Vainshtein, P., J. (1995) Aerosol Sci., 26, 575, Duhin, S. S. (1960) Colloid J., 22, 128 (In Russian), Czyz, H. (1990) Acustica 70, 23, and Vainshtein, P., Fichman, Wl., Shuster, K. and Gutfinger, C. (1996) J. Fluid Mech., 306, 3 1-42 and in the references which are cited therein, all incorporated herein by reference. The acoustic force is used to position and levitate particles, see King, L. V. (1934) Proc. Roy. Soc., 147A, 212-240, Fuchs, N. A. (1964) The Mechanics of Aerosols, Pergamon, Oxford, Coakley, W. T., Bardsley, D. W., Grundy, M. A., Zamani, F. and Clarke, D. J. (1989) J, Chem. Tech. Biotech. 44, 43, Gopinath, A. and Mills, A. F. (1994) Trans. ASME C: J. Heat Transfer, 1 16, 47-53, Hertz, H. M. (1995) J. Appl. Physics, 78, 4845-4849, and papers cited therein, all incorporated herein by reference.

Reference is now also made to FIG. 4, which is a flowchart of a method of focusing a plurality of discrete particles by applying an acoustic field, optionally quadrupole, according to some embodiments of the present invention.

First, as shown at 401, device having a capillary with a longitudinal axis, such as shown at FIG. 1, is provided. Optionally, the capillary is straight, or substantially straight.

Then, as shown at 402, a flow of a fluid medium is established within the capillary. The fluid medium carries a plurality of discrete hydrosol or aerosol particles. It should be noted that as the vibrations may be at low frequency of less than 20

Khz, for example 1 Khz, relatively sensitive particles, such as cells and Bactria may be concentrated.

Optionally, an axial gas flow is imposed in the x-direction, as shown at 105 of FIG. 1. In such an embodiment, the fluid medium is a gas-suspension flow in a capillary having an inner lumen 107 with a diameter of $2r_0=10$ mm. In such an embodiment, the diameter of the capillary 102 is equal to the distance between orifices in lens arrays, see Wang, X., Gidwani, A., Girshick, S. L. and McMurry, P. H. (2005). Aerosol Sci. Techn., 39, 624-636, which is incorporated herein by reference.

Now, as shown at 403, an acoustic field, optionally substantially quadrupole, having a central axis substantially along the longitudinal axis is applied so as to focus the discrete hydrosol and/or aerosol particles, optionally as a beam, along the longitudinal axis 105. The generated field is applied to focus aerosol and/or hydrosol particles having a diameter that ranges between about few microns and about a submicron size along the longitudinal axis 105.

The acoustic field is optionally applied by vibrating the capillary, for example as described above. Optionally, the frequency of vibration, denoted herein as f, is about 1 kHz. For such a frequency, the wavelength, denoted herein as λ, in air is 34.4 cm.

Optionally, the diameter of the capillary 102, $r_0$, and the frequency of the vibration are set so as $\lambda \gg 2r_0$. In such a manner, no standing wave is formed inside the inner lumen 107, see, for example, Vainshtein, P. B., Fichman, M., Pnueli, D. (1992) J. Aerosol Science, 23 (6), 631-657, which is incorporated herein by reference. The pressure disturbances, which are induced by the vibrating of the walls 104, generate cross-sectional acoustic waves at the channel walls 104. These pressure disturbances may be defined as follows $$p - p_0 = p_s \cos \omega t \text{ at } y^2 - z^2 = r_0^2 \quad (2); \text{ and}$$

$$p - p_0 = p_s \cos \omega t \text{ at } z^2 - y^2 = r_0^2 \quad (1)$$

where $p_s$ denotes an amplitude of pressure oscillations, $p_0$ denotes undisturbed pressure, and $\omega = 2\pi f$. Solution of the Laplace equation, satisfying the boundary conditions on the walls 104, describes the pressure distribution in the capillary cross-sections, such that the cross-sectional pressure gradient is time-varying and proportional to the distance from the longitudinal axis 105. As a result, the cross-sectional velocity field, obtained from the Navier-Stokes equations, is time-varying and vanishing at the channel axis (y=z=0). The cross-sectional velocity field may be defined as follows:

$$v = -v_s \frac{y}{r_0} \sin \omega t, \ w = v_s \frac{z}{r_0} \sin \omega t \quad \text{Equation 1}$$

where v and w denotes cross-sectional components of the fluid velocity vector, u=(u, v, w), and Equation 2

$$v_s = 2 \frac{p_s}{\rho_f \omega r_0} \quad (2)$$

where $\rho_f$ denotes the fluid density and $V_s$ denotes the characteristic amplitude of fluid velocity oscillations occurring in the channel, and $r_0$ denotes the diameter of the inner lumen of the capillary. For $r_0$, this amplitude is determined by the parameters of a sound field, namely by the frequency and amplitude of wall oscillations.

The fluid velocity V, which is defined in Equation 1, is independent of viscosity; however it satisfies the equations of the viscous flow and slip boundary condition. The latter is induced as the cross-sectional velocity vector is a normal to the channel walls 104, for example as depicted in FIG. 5, which depicts a cross sectional schematic illustration depicting fluid streamlines where the arrows show the directions of the fluid oscillations.

Figure 5:
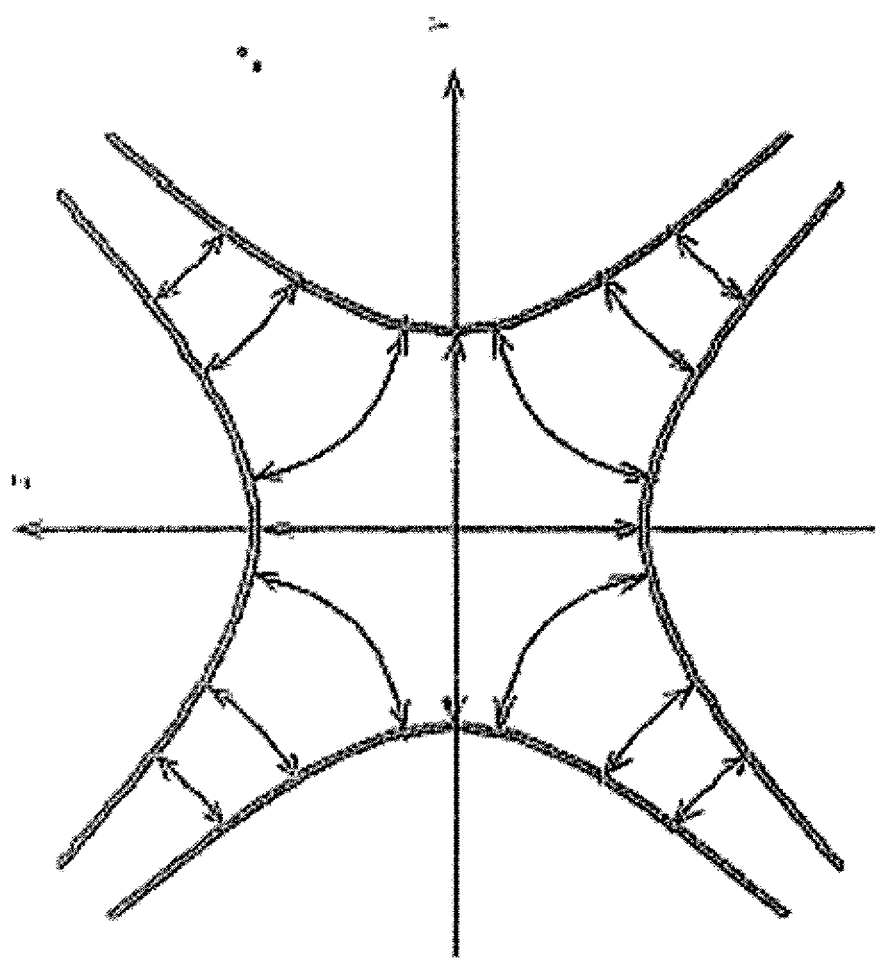
FIG. 5 is a cross sectional schematic illustration of a fluid streamlines in a capillary, where the arrows depict the directions of the fluid oscillations of the fluid streamlines, according to some embodiments of the present invention.

According to Equation 1, the fluid velocity oscillates along the streamlines depicted in FIG. 5. It is linearly distributed and vanishing at the longitudinal axis 105. This leads a particles drift which moves towards the longitudinal axis 105 and focuses in a beam therealong.

Reference is now made to the focusing effect. Optionally, the flow is a diluted aerosol so that particle-particle interactions are negligible and the presence of particles does not affect the carrier gas flow field. In this explanation, the trajectories of a rigid, non-diffusive particle of radius a in the flow field defined in Equation 1. The fluid-particle interaction may be described by a linear drag force, for example as follows:

$$\frac{du_p}{dt} = \frac{u - u_p}{\tau}, \ \tau = 2a^2 / 9v \Pi_\rho \quad \text{Equation 3}$$

where $u_p$ denotes a particle velocity vector, $\tau$ denotes a Stokes relaxation time, $\Pi_\rho$ denotes a fluid-to particle-density ratio, and $v$ denotes a fluid kinematic viscosity. Such an approximation is valid for aerosol applications when $\Pi_\rho \omega \tau \ll 1$.

Figure 6A:
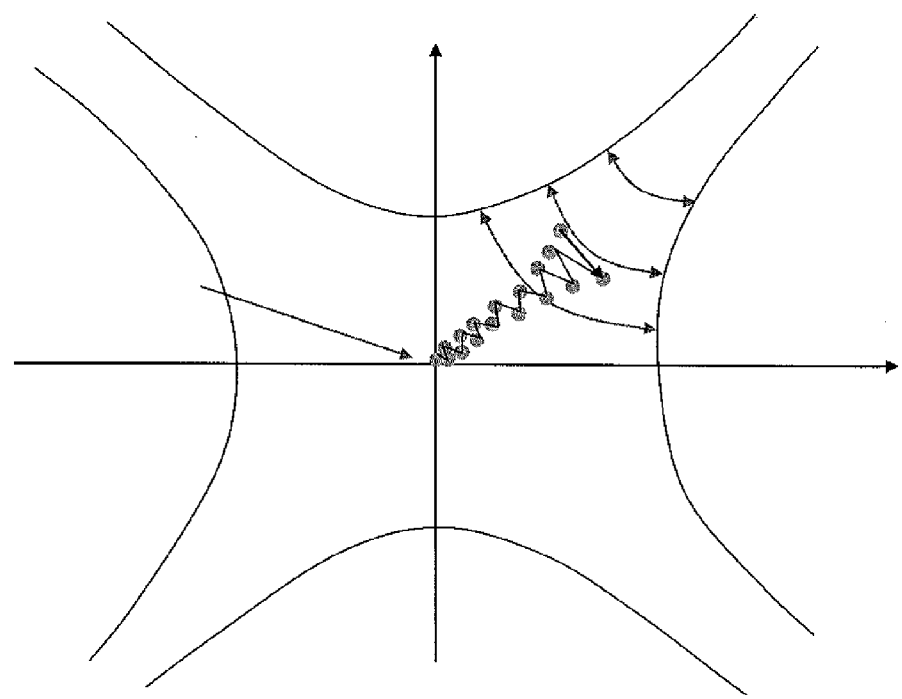
FIGS. 6A and 6B are schematic illustrations of particles' trajectories starting in an upstream region at various spatial locations along the longitudinal axis of the capillary and dynamically concentrating in a narrower region, according to some embodiments of the present invention.
Figure 6B:
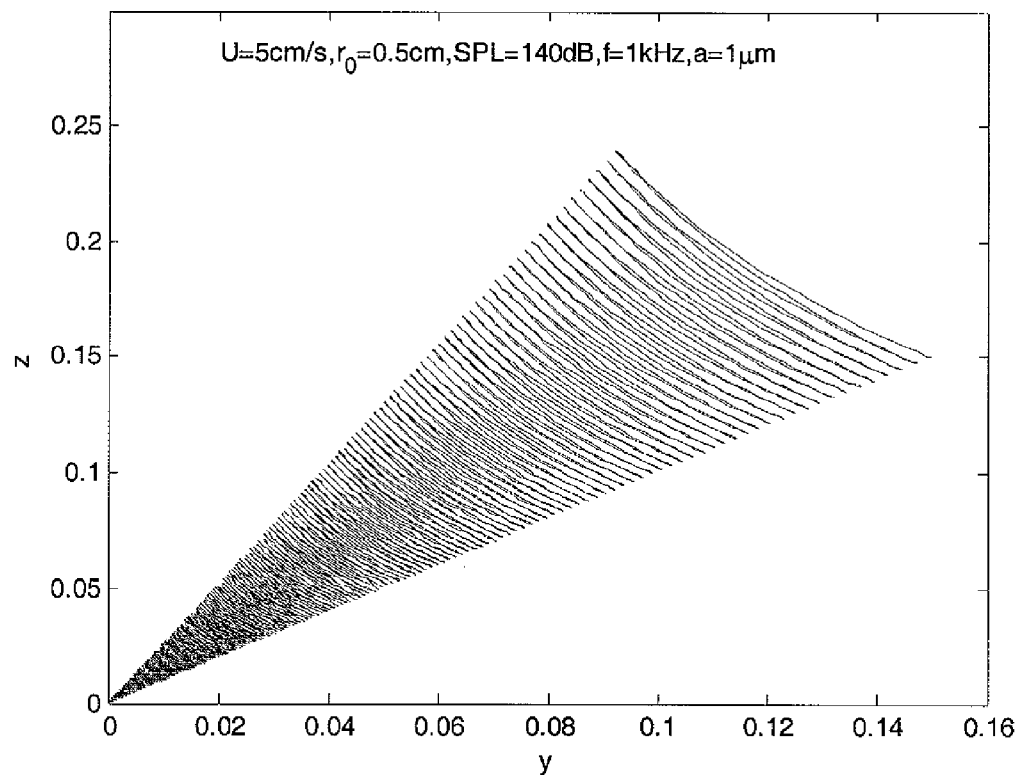

According to Equations 1-3, particles introduced into the capillary 102 move due to the differences between their velocity and the fluid medium's velocity. As a result, of the particles' trajectories starting in an upstream region at various spatial locations along the longitudinal axis 105, are dynamically concentrated to the narrower region, as shown at FIGS. 6A and 6B. This concentrating effect associated with particle inertia will lead to increase in particle concentration by several orders of magnitude.

Each particle travels in oscillating motions as the fluid velocity oscillates. However, the particle is not entrained fully in the oscillating fluid flow owing to its inertia. It deviates from the fluid streamlines, for example those shown at FIG. 5, and moves towards the longitudinal axis, optionally in converging swing motions, as shown in FIGS. 6A and 6B which respectively depict a cross-sectional schematic illustration of the capillary 102 and a trajectory of a single particle therein and a calculation of the particle cross-sectional trajectory where a particle starts from coordinates $y_0=z_0=0.15$ drifts toward coordinates x=y=0, deviating from the fluid streamlines sketched in FIGS. 5 and 6B, z and y are normalized by $r_0$. This occurs as the fluid cross-sectional velocity decreases toward the longitudinal axis 105. The particles remain in the longitudinal axis 105 as a particle moving toward the longitudinal axis is applied with a larger hydrodynamic force and passes a larger distance than a particle moving at the opposite direction. Within every oscillating period, this difference in the passing distances may be relatively small however for a large number of oscillations, the particle advances on average towards the axis. This represents a particle drifting motion.

Figure 4:
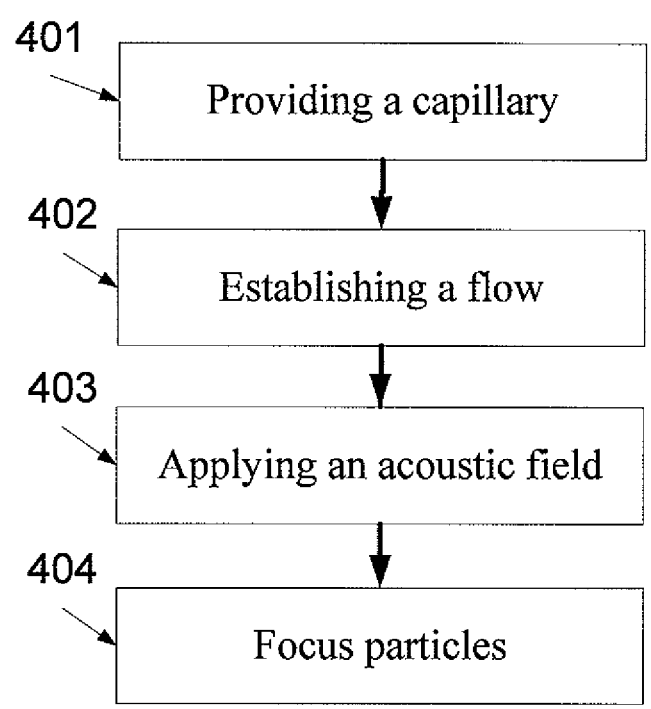
FIG. 4 is flowchart of focusing a plurality of discrete particles, according to some embodiments of the present invention.

As described above, and depicted in 402 of FIG. 4, the cross-sectional drifting motion of particles is actuated by the acoustic excitation of the channel walls 104. An imposed axial pressure gradient, in the x-direction, leads to axial fluid flow. This axial flow drives particles downstream, along the longitudinal axis 105. Axial velocity profile is described approximately by Poiseuille formula with maximal velocity U valid near the channel axis.

Figure 7:
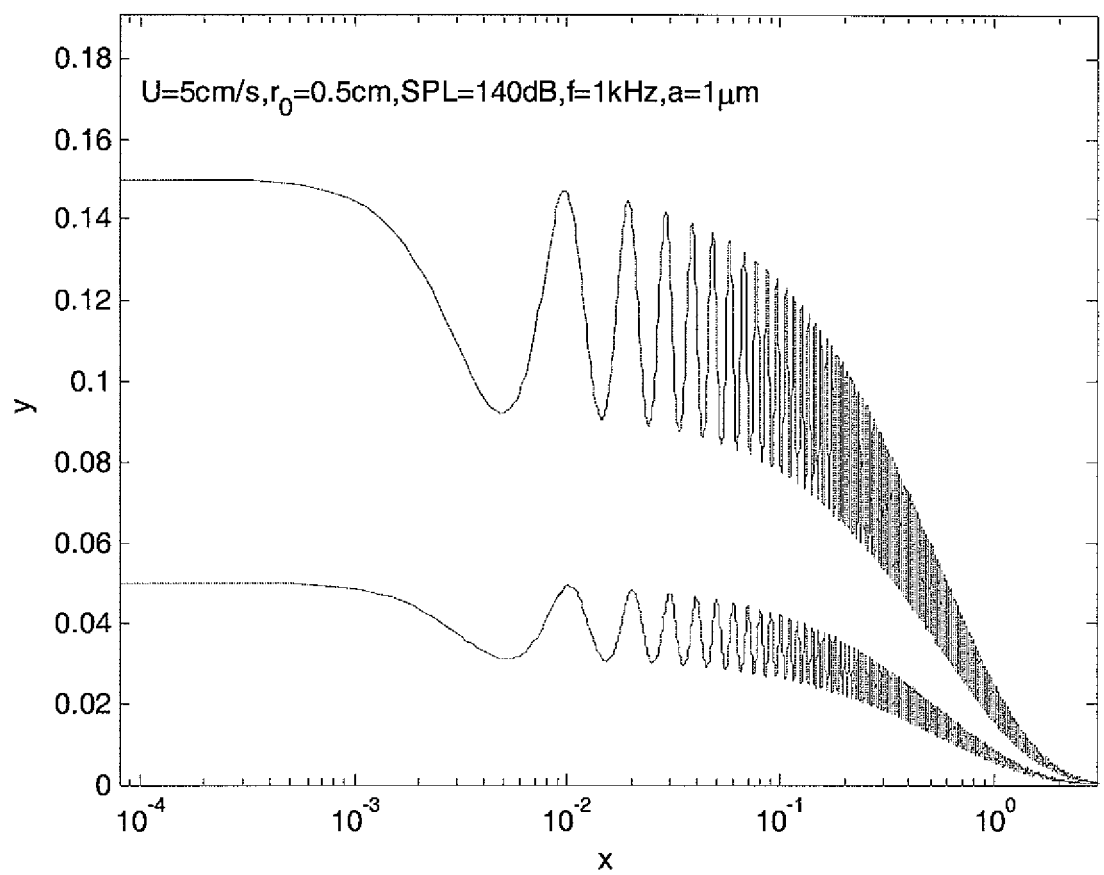
FIG. 7 is a schematic illustration of trajectories of two particles in a capillary, such as depicted in FIG. 1, when an acoustic field is applied thereon, according to some embodiments of the present invention.

Reference is now made to FIG. 7, which is a schematic illustration of trajectories of two particles in a capillary, such as 102 on which a quadrupole acoustic field is applied, according to some embodiments of the present invention. In FIG. 7, x and y are normalized by $r_0$. The trajectories in FIG. 7 are of 1 µm particles in the capillary 102. Particles are seeded at the inlet 108 of the channel, for example as shown at coordinates ($x_0=0$, $y_0=0.15$) and ($x_0=0$, $y_0=0.05$), with the initial velocity coinciding with that of air. It is seen that all particles approach steadily the longitudinal axis 105. This describes acoustic focusing. For specificity 10-fold focusing is considered when particle's ordinate falls ten times. The corresponding time $t_{1/10}$ and the distance $x_{1/10}$ characterize focusing efficiency. It is seen that for the data depicted in FIG. 7, 10-fold focusing occurs in about one radius distance.

Optionally, as outlined above, the device 100 is unpartitioned and therefore does not have spatially periodic configuration. In such embodiments, the device 100 may be used to deliver the particles at atmospheric pressure, at relatively high Reynolds numbers, as losses connected with particle mixing pertinent are avoided. The Reynolds numbers are high relative to the Reynolds numbers of focusing spatially periodic aerodynamic lens arrays. As the Reynolds numbers are relatively high, the particle transmission rate is respectively relatively high.

According to some embodiments of the present invention, the device 100 is used to focus particles in an inlet of an on-line single-particle analyzer, such as an aerosol mass spectrometer and/or any analytical chemistry analyzer, such as atmospheric science, biological detection, pharmaceutical manufacturing, and/or engine research.

According to some embodiments of the present invention, the device 100 is employed in combination with aerodynamic lens arrays. In such embodiments, the device 100 is used as an acoustic lens channel of some or all of the stages of a lens array. In such a manner, the particles concentration on each stage is enhanced and consequently the size of the orifices may be decreased, reducing the pumping costs.

It is expected that during the life of a patent maturing from this application many relevant devices and methods will be developed and the scope of the term a capillary, a pump, and a vibration source is intended to include all such new technologies a priori.

As used herein the term "about" refers to ±10.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device of focusing a plurality of particles, comprising:
    a capillary having a longitudinal axis and a substantially unpartitioned lumen to flow a fluid medium having a plurality of particles; and
    at least one vibration source for vibrating said capillary in a frequency of less than 10 Mega Hertz (MHz) so as to focus said plurality of particles along said longitudinal axis;
    wherein said capillary having a plurality of separate walls and a plurality of slits, each said slit being formed between each adjacent pair of walls of said plurality of separate walls.

2. The device of claim 1, wherein said inner lumen having a diameter of about 10 millimeter.

3. The device of claim 1, wherein said plurality of separate walls are separated from one another.

4. The device of claim 1, wherein each said vibration source is connected to vibrate one of said plurality of separate walls.

5. The device of claim 1, wherein each separate wall is convex toward a longitudinal axis of said capillary.

6. The device of claim 1, wherein each separate wall is concave toward a longitudinal axis of said capillary.

7. The device of claim 1, wherein said at least one vibration source comprises a plurality of vibration sources arranged to vibrate said capillary so as to form a quadrupole acoustic field having a central axis substantially along a longitudinal axis of said capillary.

8. The device of claim 1, wherein said capillary having four plurality of separate walls arranged to form a cylindrical lumen.

9. An aerodynamic lens array having the device of claim 1 as a lens in at least one stage.

10. A single-particle analyzer having the device of claim 1 for focusing said plurality of particles before an analysis thereof.

\* \* \* \* \*